United States Patent
Lai et al.

(10) Patent No.: US 10,195,816 B2
(45) Date of Patent: Feb. 5, 2019

(54) METAL/POLYMER COMPOSITE MATERIAL AND METHOD FOR FABRICATING THE SAME

(71) Applicant: INDUSTRIAL TECHNOLOGY RESEARCH INSTITUTE, Hsinchu (TW)

(72) Inventors: Hong-Jen Lai, Hsinchu (TW); Ming-Sheng Leu, Zhudong Township (TW); Tai-Sheng Chen, Kaohsiung (TW); Wei-Tien Hsiao, Zhudong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/586,171

(22) Filed: Dec. 30, 2014

(65) Prior Publication Data
US 2016/0153081 A1 Jun. 2, 2016

(30) Foreign Application Priority Data
Dec. 1, 2014 (TW) ............... 103141581 A

(51) Int. Cl.
| | |
|---|---|
| B32B 3/28 | (2006.01) |
| C23C 16/02 | (2006.01) |
| C23C 14/02 | (2006.01) |
| B32B 15/08 | (2006.01) |
| A61L 27/56 | (2006.01) |

(Continued)

(52) U.S. Cl.
CPC ............... *B32B 3/28* (2013.01); *A61L 27/56* (2013.01); *B32B 15/08* (2013.01); *C23C 14/028* (2013.01); *C23C 14/20* (2013.01); *C23C 16/0254* (2013.01); *C23C 16/06* (2013.01);

(Continued)

(58) Field of Classification Search
CPC ........................................................ B32B 3/28
See application file for complete search history.

(56) References Cited

U.S. PATENT DOCUMENTS 3,868,229 A 2/1975 Hurley
4,012,795 A * 3/1977 Dorre .................... A61F 2/3609
623/22.46

(Continued)

FOREIGN PATENT DOCUMENTS

CN 101128166 A 2/2008
CN 102574362 A 7/2012

(Continued)

OTHER PUBLICATIONS

Achour et al., "Stress Distribution in Dental Implant with Elastomeric Stress Barrier", Materials and Design, vol. 32, 2011, pp. 282-290.

(Continued)

*Primary Examiner* — Z. Jim Yang
(74) *Attorney, Agent, or Firm* — Birch, Stewart, Kolasch & Birch, LLP

(57) ABSTRACT

A metal/polymer composite material is disclosed, wherein the metal/polymer composite material comprises a polymer base and a metal heat-dissipation layer. The heat-dissipation layer comprises a roughed surface with an isotropic surface roughness. The metal heat-dissipation conformally blankets over the roughed surface.

7 Claims, 3 Drawing Sheets

(51) Int. Cl.
 *C23C 14/20* (2006.01)
 *C23C 16/06* (2006.01)
(52) U.S. Cl.
 CPC .. *Y10T 428/1241* (2015.01); *Y10T 428/12993* (2015.01); *Y10T 428/24545* (2015.01)

(56) References Cited

U.S. PATENT DOCUMENTS

| | | | |
|---|---|---|---|
| 4,411,943 A * | 10/1983 | Akao | G11B 23/08764 428/161 |
| 4,483,785 A | 11/1984 | Johnson et al. | |
| 4,642,163 A * | 2/1987 | Greschner | B29C 59/14 204/192.3 |
| 5,201,766 A * | 4/1993 | Georgette | A61F 2/30767 128/898 |
| 5,370,698 A * | 12/1994 | Heimke | A61F 2/30767 623/22.15 |
| 5,879,398 A * | 3/1999 | Swarts | A61F 2/30907 623/22.21 |
| 6,074,740 A | 6/2000 | Scheckenbach et al. | |
| 6,126,695 A * | 10/2000 | Semlitsch | A61F 2/30767 623/18.11 |
| 6,602,293 B1 | 8/2003 | Biermann et al. | |
| 6,800,073 B2 | 10/2004 | Palasis et al. | |
| 7,060,056 B2 | 6/2006 | Palasis et al. | |
| 7,189,409 B2 | 3/2007 | Pirhonen et al. | |
| 7,285,331 B1 * | 10/2007 | Reihs | B05D 5/08 427/435 |
| 7,875,075 B2 | 1/2011 | Schwab | |
| 8,128,700 B2 | 3/2012 | Delurio et al. | |
| 8,303,879 B2 | 11/2012 | Bertele et al. | |
| 8,323,722 B2 | 12/2012 | Rabiei | |
| 8,361,150 B2 | 1/2013 | Zhang et al. | |
| 8,414,650 B2 | 4/2013 | Bertele et al. | |
| 8,420,181 B2 | 4/2013 | Kim | |
| 8,425,604 B2 | 4/2013 | Trieu | |
| 8,470,042 B2 | 6/2013 | Zhang et al. | |
| 8,603,174 B2 | 12/2013 | Haines | |
| 9,522,820 B2 * | 12/2016 | Khine | B81C 1/00071 |
| 9,782,268 B2 * | 10/2017 | Aeschlimann | A61B 17/0401 |
| 2005/0037916 A1 * | 2/2005 | Chen | B29C 33/42 502/101 |
| 2005/0049716 A1 * | 3/2005 | Wagener | A61F 2/30767 623/23.5 |
| 2006/0202385 A1 * | 9/2006 | Xu | A61M 37/0015 264/219 |
| 2007/0026197 A1 * | 2/2007 | Suga | B29C 45/14811 428/172 |
| 2008/0015616 A1 * | 1/2008 | Ricci | A61B 17/68 606/151 |
| 2008/0107890 A1 | 5/2008 | Bureau et al. | |
| 2008/0125510 A1 * | 5/2008 | Crosby | C08F 265/04 522/99 |
| 2008/0157235 A1 * | 7/2008 | Rogers | H01L 21/8258 257/415 |
| 2009/0084491 A1 * | 4/2009 | Uthgenannt | A61F 2/389 156/153 |
| 2009/0220561 A1 * | 9/2009 | Jin | A61K 9/0009 424/423 |
| 2009/0276053 A1 | 11/2009 | Brown et al. | |
| 2010/0023057 A1 * | 1/2010 | Aeschlimann | A61B 17/0401 606/246 |
| 2010/0062590 A1 | 3/2010 | Lin et al. | |
| 2010/0092754 A1 | 4/2010 | Nishida et al. | |
| 2010/0137990 A1 * | 6/2010 | Apatsidis | A61B 17/866 623/17.16 |
| 2010/0256773 A1 * | 10/2010 | Thijs | A61C 8/0006 623/23.55 |
| 2010/0262244 A1 | 10/2010 | Savage-Erickson et al. | |
| 2010/0304065 A1 * | 12/2010 | Tomantschger | B32B 15/08 428/35.8 |
| 2011/0039086 A1 * | 2/2011 | Graham | A61L 27/04 428/220 |
| 2011/0060399 A1 * | 3/2011 | Charlebois | A61L 31/022 623/1.15 |
| 2011/0125284 A1 * | 5/2011 | Gabbrielli | A61F 2/30767 623/23.4 |
| 2011/0153028 A1 | 6/2011 | Albertorio | |
| 2011/0287203 A1 * | 11/2011 | Victor | B29C 37/0053 428/36.9 |
| 2012/0010599 A1 | 1/2012 | Jin et al. | |
| 2012/0187406 A1 | 7/2012 | Tsai et al. | |
| 2012/0221110 A1 * | 8/2012 | Nakanishi | A61F 2/30771 623/18.11 |
| 2012/0277861 A1 | 11/2012 | Steele et al. | |
| 2012/0277869 A1 | 11/2012 | Siccardi et al. | |
| 2013/0096689 A1 | 4/2013 | Lowry et al. | |
| 2013/0119487 A1 | 5/2013 | Lin et al. | |
| 2013/0131699 A1 | 5/2013 | Jiang et al. | |
| 2013/0153824 A1 | 5/2013 | Meehan et al. | |
| 2013/0166028 A1 | 6/2013 | Shieh et al. | |
| 2013/0218288 A1 | 8/2013 | Fonte et al. | |
| 2014/0302279 A1 * | 10/2014 | Pfaffelhuber | B32B 3/26 428/138 |
| 2014/0363631 A1 * | 12/2014 | Gong | B32B 15/08 428/164 |
| 2015/0012100 A1 * | 1/2015 | Ullrich, Jr. | A61F 2/4465 623/17.16 |
| 2016/0135958 A1 * | 5/2016 | Grostefon | A61F 2/32 623/22.18 |
| 2016/0155537 A1 * | 6/2016 | Manabe | H01B 7/045 174/107 |

FOREIGN PATENT DOCUMENTS

| | | | | |
|---|---|---|---|---|
| CN | 202617335 U | 12/2012 | | |
| CN | 103200887 A | 7/2013 | | |
| CN | 103242551 A | 8/2013 | | |
| CN | 104921845 A | 9/2015 | | |
| EP | 1 175 949 A1 | 1/2002 | | |
| EP | 2 435 602 A1 | 4/2012 | | |
| EP | 2 641 621 A1 | 9/2013 | | |
| EP | 2 526 977 B1 | 2/2014 | | |
| EP | 2762172 A1 * | 8/2014 | | B32B 7/12 |
| JP | 5-131005 A | 5/1993 | | |
| JP | 2011-143539 A | 7/2011 | | |
| TW | 280767 B | 7/1996 | | |
| TW | 200708295 A | 3/2007 | | |
| TW | I302372 B | 10/2008 | | |
| TW | 200902610 A | 1/2009 | | |
| TW | I321372 B | 3/2010 | | |
| TW | I346253 B | 8/2011 | | |
| TW | 201232783 A | 8/2012 | | |
| TW | I376734 B | 11/2012 | | |
| TW | 201320331 A | 5/2013 | | |
| TW | I423782 B | 1/2014 | | |
| TW | I448270 B | 8/2014 | | |
| WO | WO 2006/063354 A1 | 6/2006 | | |
| WO | WO 2012/110816 A1 | 8/2012 | | |
| WO | WO 2014/072983 A1 | 5/2014 | | |

OTHER PUBLICATIONS

Amanat et al. "Gas Permeability Reduction in PEEK Film: Comparison of Tetrahedral Amorphous Carbon and Titanium Nanofilm Coatings", Journal of Membrane Science, vol. 378, 2011 pp. 265-271.

Breguet et al., "Compact, Light Weight Mechanisms for High Precision Micro-Manipulators", Swiss Federal Institute of Technology Lausanne (EPFL), Switzerland, Sep. 1999, 5 pages.

Chen et al., "Numerical Simulation of Two-Dimensional Melting and Resolidification of a Two-Component Metal Powder Layer in Selective Laser Sintering Process", Numerical Heat Transfer, Part A, vol. 46, 2004, pp. 633-649.

Chen et al., "Three-Dimensional Modeling of Laser Sintering of a Two-Component Metal Powder Layer on Top of Sintered Layers", Journal of Manufacturing Science and Engineering, vol. 129, Jun. 2007, pp. 575-582.

(56) References Cited

OTHER PUBLICATIONS

Contuzzi et al., "3D Finite Element Analysis in the Selective Laser Melting Process", Int J Simul Model, vol. 10, No. 3, 2011, pp. 113-121.
Devine et al. "Coating of Carbon Fiber-Reinforced Polyetheretherketone Implants with Titanium to Improve Bone Apposition", Society for Biomaterials, Published online Dec. 20, 2012, pp. 591-598.
Du et al., "Plastic Forming Simulations of Cold Isostatic Pressing of Selective Laser Sintered Components", Transactions of Nonferrous Metals Society of China, vol. 21, 2011, pp. 1118-1122.
Facchini et al., "Ductility of a Ti—6Al—4V Alloy Produced by Selective Laser Melting of Prealloyed Powders", Rapid Prototyping Journal, vol. 16, No. 6, 2010, pp. 450-459, plus 3 additional pages.
Fan et al., "Numerical Modeling of the Additive Manufacturing (AM) Processes of Titanium Alloy", Titanium Alloys—Towards Achieving Enhanced Properties for Diversified Applications, Intech, Published Online Mar. 16, 2012 (Published in Print Mar. 2012), pp. 3-28, plus cover page.
Han et al., "Fabrication of Gear Having Functionally Graded Properties by Direct Laser Melting Process", Advances in Mechanical Engineering, vol. 2014, Article ID 618464, published Apr. 9, 2014, pp. 1-6, plus 1 additional page.
Han et al., "The Electron Beam Deposition of Titanium on Polyetheretherketone (PEEK) and the Resulting Enhanced Biological Properties", Biomaterials, vol. 31, 2010, pp. 3465-3470.
Hsu et al., "Parametric Study on the Interface Pullout Strength of the Vertebral Body Replacement Cage Using FEM-Based Taguchi Methods", Medical Engineering & Physics, vol. 31, 2009, pp. 287-294.
Kolossov et al., "3D FE Simulation for Temperature Evolution in the Selective Laser Sintering Process", International Journal of Machine Tools & Manufacture, vol. 44, 2004, pp. 117-123.
Laurens et al., "Enhancement of the Adhesive Bonding Properties of PEEK by Excimer Laser Treatment", International Journal of Adhesion & Adhesives, vol. 18, 1998, pp. 19-27.
Lin et al., "Structural and Mechanical Evaluations of a Topology Optimized Titanium Interbody Fusion Cage Fabricated by Selective Laser Melting Process", Journal of Biomedical Materials Research, vol. 83, Part A, 2007, Published Online Apr. 5, 2007, pp. 272-279.
Maurer et al., "Erosion Resistant Titanium Based PVD Coatings on CFRP", Wear, vol. 302, 2013, pp. 937-945.
Mikos et al., "Laminated Three-Dimensional Biodegradable Foams for Use in Tissue Engineering", Biomaterials, vol. 14, No. 5, 1993, pp. 323-330.
Roberts et al., "A Three-Dimensional Finite Element Analysis of the Temperature Field During Laser Melting of Metal Powders in Additive Layer Manufacturing", International Journal of Machine Tools & Manufacture, vol. 49, 2009, pp. 916-923.
Seyda et al., "Investigation of Aging Processes of Ti—6Al—4V Powder Material in Laser Melting", Physics Procedia, vol. 39, 2012, pp. 425-431.
Sumner et al., "Functional Adaptation and Ingrowth of Bone Vary as a Function of Hip Implant Stiffness", Journal of Biomechanics, vol. 31, 1998, pp. 909-917.
Wu et al. "Investigation of Hydroxyapatite Coated Polyether Ether Ketone Composites by Gas Plasma Sprays", Surface & Coatings Technology, vol. 203, 2009, pp. 2755-2758.
Wu et al., "Porous Titanium-6 Aluminum-4 Vanadium Cage Has Better Osseointegration and Less Micromotion Than a Poly-Ether-Ether-Ketone Cage in Sheep Vertebral Fusion", Artificial Organs, vol. 37, No. 12, 2013, pp. E191-E201.
Xiao et al., "Topology Optimization of Microstructure and Selective Laser Melting Fabrication for Metallic Biomaterial Scaffolds", Transactions of Nonferrous Metals Society of China, vol. 22, 2012, pp. 2554-2561.
Zhong et al., "Finite Element Analysis of the Lumbar Spine with a New Cage Using a Topology Optimization Method", Medical Engineering & Physics, vol. 28, 2006, pp. 90-98.
Taiwan Office Action dated Sep. 17, 2015 for Appl. No. 103141581.
Polyaryletherketone data sheet. Obtained from https://plastics.ulprospector.com on Sep. 20, 2017.
U.S. Office Action dated Feb. 14, 2018 for U.S. Appl. No. 14/981,325.

\* cited by examiner

METAL/POLYMER COMPOSITE MATERIAL AND METHOD FOR FABRICATING THE SAME

This application claims the benefit of Taiwan application Serial No. 103141581, filed Dec. 1, 2014, the disclosure of which is incorporated by reference herein in its entirety.

TECHNICAL FIELD

The disclosure relates in general to a composite material and method for fabricating the same, and more particularly to a metal/polymer composite material and method for fabricating the same.

BACKGROUND

Polymer material, such as polyether ether ketone (PEEK), polymethyl methacrylate (PMMA), polyethylene terephthalate (PET), polylactide (PLA), polytetrafluoroethene (PTFE), possessing excellent mechanical properties and chemical resistance, anti-wear, hydrolysis resistance and other properties, have now been widely used in various fields such as medical implant apparatus, semi-conductor process, aeronautical engineering, and precision machinery.

Lacking sufficient support strength and heat resistance, in subsequent machining process, the polymer material may easily deteriorate due to high temperature. Particularly, when the polymer material and the metal material are combined to form a composite material possessing the properties of both the polymer material and the metal material, the polymer material at the heterojunction between the two materials may be easily damaged due to high temperature and cause the metal material to be peeled off the polymer material, greatly affecting the performance and application of the composite material. Therefore, an advanced metal/polymer composite material and method for fabricating the same are required for resolving the problems encountered in generally known technology.

Therefore, a metal/polymer composite material method for fabricating the same and applications thereof are required for resolving the problems encountered in generally known technology.

SUMMARY

The disclosure is directed to a metal/polymer composite material comprising a polymer base and a metal heat-dissipation layer. The polymer base has a roughed surface with an isotropic surface roughness. The metal heat-dissipation layer conformally blankets over the roughed surface.

According to one embodiment, a method for fabricating a metal/polymer composite material is provided. The method comprises following steps: Firstly, a polymer base is provided. Next, a surface roughening process is performed to form a roughed surface with an isotropic surface roughness on the polymer base. Then, a metal heat-dissipation layer conformally blanketing over the roughed surface is formed.

According to another embodiment of the present disclosure, a metal/polymer composite material with heterojunction and a method for fabricating the same are provided. Firstly, a surface roughening treatment is performed to form a roughed surface with non-directional roughness on the polymer base. Then, a metal heat-dissipation layer conformally blanketing over the roughed surface is formed.

The embodiments of the disclosure are provided to resolve the problems encountered in conventional technology. Since the metal heat-dissipation layer is formed on the polymer base by using a low-temperature coating (deposition) technology, the metal heat-dissipation layer will not cause damage to the polymer base. Furthermore, the metal heat-dissipation layer conformally blankets over a roughed surface with an isotropic surface roughness, such that the metal heat-dissipation layer and the polymer base can be tightly bonded at the heterojunction. Therefore, in subsequent high temperature process, the problem of the metal heat-dissipation layer being peeled off due to the polymer material layer being damaged by the concentration and penetration of thermal stress can be avoided, and the performance of the metal/polymer composite material can be improved.

To summarize, the metal/polymer composite material and the method for fabricating the same provided in the disclosure not only resolves the problems encountered in convention technology but at the same time overcomes the restrictions and drawbacks of the metal/polymer composite material currently available, so as to achieve the objects of the disclosure. In the conventional technology, the problems stress concentration and insufficient elasticity will occur if the metal material alone is used, and the problem of the supporting strength being too weak will occur if the polymer material alone is used.

The above and other aspects of the invention will become better understood with regard to the following detailed description of the preferred but non-limiting embodiment (s). The following description is made with reference to the accompanying drawings.

BRIEF DESCRIPTION OF THE DRAWINGS

FIG. 1 A to FIG. 1 C are structural cross-sectional views of the processes for fabricating the metal/polymer composite material according to FIG. 1.

Figure 1:
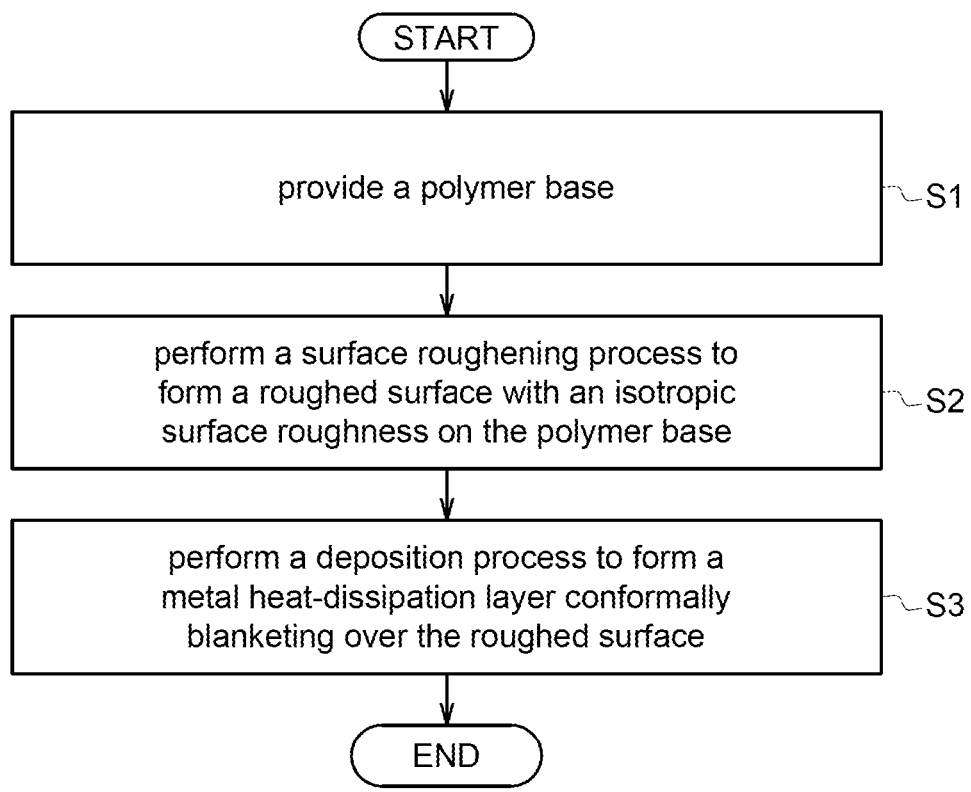
FIG. 1 is a flowchart of a method for fabricating a metal/polymer composite material according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

The embodiments disclosed in the present specification relate to a metal/polymer composite material, a method for fabricating the same and applications thereof capable of resolving the problems encountered in conventional technology and derived from the concentration and penetration of thermal stress which damages the polymer material layer and causes the metal material to peel off. For the above objects, features and advantages of the present disclosure to be clearly understood, a method for fabricating a metal/polymer composite material with hetero-junction, and a medical composite material using the metal/polymer composite material are disclosed in an exemplary embodiment, and detailed descriptions are disclosed below with accompanying drawings.

However, it should be noted that the embodiments and methods exemplified in the present disclosure are not for limiting the scope of protection of the present disclosure. The present disclosure can be implemented by using other features, methods and parameters. Exemplary embodiments are disclosed for exemplifying the technical features of the present disclosure, not for limiting the scope of protection of the present disclosure. Anyone who is skilled in the technology field of the disclosure can make necessary modifications or variations according to the descriptions of the present specification without violating the spirit of the present disclosure. For the same components common to different embodiments and drawings, the same numeric designations are retained.

Figure 1A:
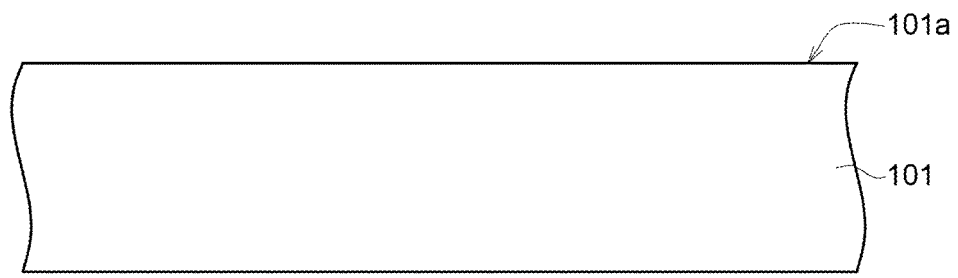
Figure 1B:
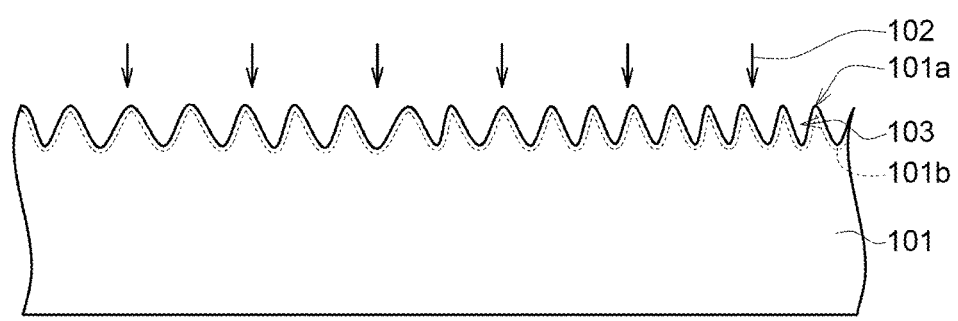
Figure 1C:
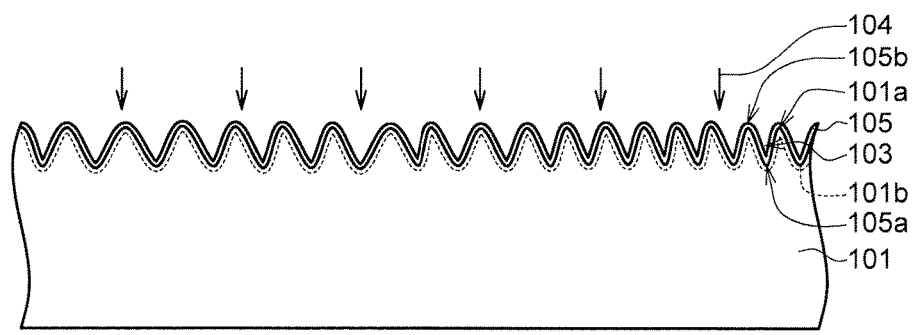

FIG. 1 is a flowchart of a method for fabricating a metal/polymer composite material 100 according to an embodiment of the present disclosure. FIG. 1A to FIG. 1C are structural cross-sectional views of the method for fabricating a metal/polymer composite material 100 of FIG. 1. Firstly, the method for fabricating the metal/polymer composite material 100 begins at step S1, a polymer base 101 is provided (as indicated in FIG. 1A). The polymer base 101 can be formed of a polymer compound using a plasticized polymer such as plastic, silicone, synthetic rubber, synthetic fibers, synthetic paint or adhesive as the base, or a natural polymer compound comprising cellulose, starch, and protein.

In some embodiments of the present disclosure, the polymer base 101 can be formed by performing injection, pultrusion, membrane pressing, thermal pressing, blow molding, molding, filament winding, prepreg material laminating, transferring, foaming, casting, or lamination on a thermoplastic plastic, such as polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), or a thermosetting plastic, such as epoxy, phenolic, polyimide, melamine formaldehyde resin.

In the present embodiment, the polymer base 101 is formed of a polymer comprising polyether ether ketone (PEEK), carbon reinforced (PEEK), polyetherketoneketone (PEKK), polyaryletherketone (PAEK) or a combination thereof. The properties of the polymer base 101 are similar to that of human bones. For example, the polymer base 101 preferably has an elastic modulus substantially ranging from 2 Gpa to 22 Gpa.

It should be noted that the polymer base 101 used in the present disclosure is not limited thereto, and any polymer material suitable for contacting biological tissues are within the spirit of the present disclosure. In some embodiments, the polymer base 101 can be formed of other polymer material according to the biological properties applicable to the metal/polymer composite material 100.

In step S2, a surface roughening process 102 is performed to form a plurality of recesses 103 on a surface 101a of the polymer base 101, wherein each recess 103 has an aspect ratio substantially ranging from 1 to 4000 (as indicated in FIG. 1B). In some embodiments of the present disclosure, the surface roughening process 102 removes a part of the polymer base 101 by way of CNC processing, laser surface treatment, plasma surface treatment, etching or a combination thereof to form a plurality of openings or grooves (not illustrated) extending to the polymer base 101 from the surface 101a.

In some other embodiments of the disclosure, the surface roughening process 102 can be a sand blasting treatment. The sand blasting treatment uses a wind pressure substantially ranging from 1 Kg/mm2 to 5 Kg/mm2 to drive chemical non-active micro-particles such as aluminum oxide ($Al_2O_3$) particles and silicon dioxide ($SiO_2$) particles or a combination thereof (not illustrated) to physically collide with the surface 101a of the polymer base 101, so as to form a plurality of recesses 103 with controllable and uniform dimensions on the surface 101a of the polymer base 101. The aspect ratio of each recess 103 preferably ranges from 1 to 4000. Since the polymer base 101 is collided by chemical non-active micro-particles, a compact dense area 101b is normally formed under the surface 101a of the polymer base 101 after the sand blasting treatment is performed.

The recesses 103 will make the surface 101a of the polymer base 101 have an isotropic or an anisotropic surface roughness. For example, in some embodiments of the disclosure, the recesses 103 can be arranged in an irregular manner to form a 3D array pattern on the roughed surface 101a of the polymer base 101. Since the recesses 103 are directional and are irregularly arranged in the 3D array pattern, the substantially identical shear strength can measured only along a particular direction. Therefore, the roughed surface 101a of the polymer base 101 can have an anisotropic surface roughness.

In some other embodiments of the disclosure, the recesses 103 can be irregularly arranged to form an irregular 3D pattern on the roughed surface 101a of the polymer base 101. Since the recesses 103 are non-directional and are irregularly distributed, the shear strength measured on the roughed surface 101a of the polymer base 101 in different directions will substantially be identical. Therefore, the polymer base 101 can have an isotropic (non-directional) roughness. In the present embodiment, the roughed surface 101a of the polymer base 101 is a roughed surface with an isotropic roughness, and has an average surface roughness (Ra) substantially ranging from 1 μm to 5 μm.

In step S3, a metal heat-dissipation layer 105, formed by the deposition process 104, conformally blanket the roughed surface 101a of the polymer base 101 and interposes the recesses 103 to complete the fabrication of the metal/polymer composite material 100. The metal heat-dissipation layer 105 has a first surface 105a and a second surface 105b opposite to the first surface 105a. The first surface 105a contacts the roughed surface 101a of the polymer base 101, and both of the first surface 105a and the second surface 105b extend into the recesses 103 of the polymer base 101 to form a plurality of protrusions 105c in the recesses 103 (as indicated in FIG. 1C). Since the metal heat-dissipation layer 105 conformally blankets the roughed surface 101a of the polymer base 101, each protrusion 105c has an aspect ratio substantially ranging from 1 to 4000.

The shape and arrangement of the protrusions 105c correspond to that of the recess 103. For example, the protrusions 105c can be arranged in a regular or an irregular manner according to the arrangement of the micro-structures on the roughed surface 101a of the polymer base 101. The shape of each protrusion 105c corresponds to the shape of the opening of the corresponding recess 103. For example, the shape of the protrusion 105c can be an island structure, a tooth structure, a barb structure, a dove-shaped groove structure, a columnar structure or a combination thereof.

The deposition process 104 may comprise (but is not limited to) physical vapor deposition (PVD), chemical vapor deposition (CVD), arc ion plating (AIP), sputtering deposition, arc spraying), flame spray, electroplating, powder plasma spray, electroless plating, powder plasma spraying, laser powder deposition, casting, curing colloidal solution or a combination thereof.

The metal heat-dissipation layer 105 can be a single- or multi-layered structure. For example, in some embodiments of the present disclosure, the metal heat-dissipation layer 105 comprises at least one layer of metal film formed of titanium (Ti), titanium alloy (Ti-6Al-4V), cobalt-chromium alloy (Co—Cr), stainless steel (SUS 316L), gold (Au), or a combination thereof. The thickness of the metal heat-dissipation layer 105 substantially ranges from 30 μm to 500 μm. In some embodiments of the present disclosure, the thickness of the metal heat-dissipation layer 105, measured from the roughed surface 101a of the polymer base 101, preferably is greater than 150 μm.

In the present embodiment, the metal heat-dissipation layer 105 is formed by using the high power ion plating process (such as arc ion plating process) in conjunction with the synthetic powder granulation technology. A low temperature (such as 150° C.) air plasma spray (APS) is performed on a titanium metal powder so as to form at least one layer of titanium metal coating on the roughed surface 101a of the polymer base 101.

In some embodiments of the disclosure, the D50 granularity of the metal powder used in the deposition process 104 substantially ranges from 5 μm to 70 μm. The shape of the metal powder can be linear, sheet or other 3D structures distributed in a regular or irregular manner or polyhedral or spherical particles distributed in a regular or irregular manner. In the present embodiment, powder plasma spray process is preferably performed on Ti—Al—V alloy fine spherical powder whose purity is above 99% and D50 granularity substantially is less than 30 μm (such as 26 μm) under the conditions that the argon gas flow rate substantially ranges from 20 l/min to 100 l/min, the hydrogen gas flow rate substantially ranges from 1 l/min to 20 l/min and the powder carrier gas flow rate substantially ranges from 1 l/min to 5 l/min. Through gradual coating, a multi-layer titanium metal film whose thickness is substantially greater than 1 μm is formed on the roughed surface 101a of the polymer base 101 to form a metal heat-dissipation layer 105.

Since the atoms of the titanium metal have smaller particles, the heat required for forming the particles with high energy (>20 eV) and high ionization (>90%) during the melting process can be reduced. Therefore, the surface temperature (<120° C.) of the polymer base 101 during the plating process can be reduced, the damage caused by the melting powder colliding with the roughed surface 101a of the polymer base 101 can be reduced, and the adhesion between the metal heat-dissipation layer 105 and the polymer base 101 can be enhanced.

Moreover, the metal heat-dissipation layer 105 generates a thermal diffusion and buffer effect which avoids the heat being accumulated on the roughed surface 101a of the polymer base 101 in subsequent process. When the thickness of the metal heat-dissipation layer 105 reaches a certain level, such as greater than 150 μm, the temperature on the roughed surface 101a of the polymer base 101 can be reduced to be below the melting point thereof to avoid thermal stress being concentrated in subsequent process and penetrating and damaging the polymer base 101.

Besides, the titanium metal film conformally contacts and interposes the recesses 103 of the polymer base 101 to form a plurality of protrusions 105c with controllable and uniform dimensions to uniformly disperse the mechanic stress applied on the polymer base 101 via the metal heat-dissipation layer 105 and avoid the metal heat-dissipation layer 105 and the polymer base 101 being peeled off by an external force.

Figure 2:
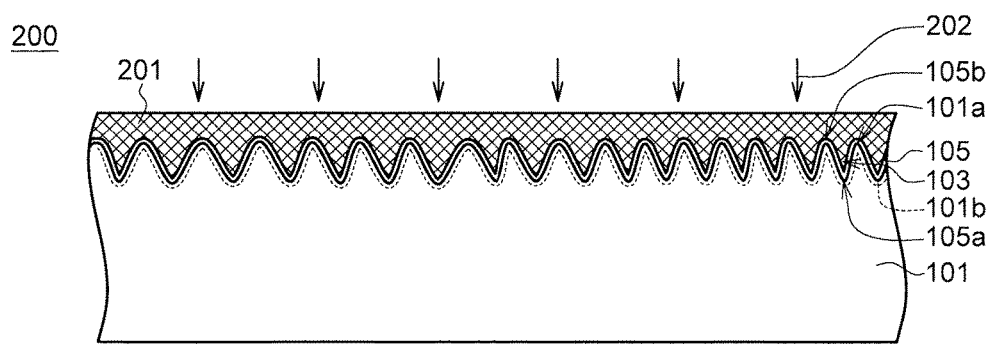
FIG. 2 is a structural cross-sectional view of a medical implant apparatus formed by using a metal/polymer composite material according to an embodiment of the disclosure.

Let the metal/polymer composite material 100 used in a medical implant apparatus be taken for example. Referring to FIG. 2, a structural cross-sectional view of a medical implant apparatus formed by using a metal/polymer composite material according to an embodiment of the disclosure is shown. The medical implant apparatus 200 uses the metal/polymer composite material 100 as the base, and subsequently in a fused deposition modeling process, an energy beam 202 (such as laser, electron beam, arc, plasma, electromagnetic conduction) is guided to sinter a metal powder by way of sintering curing, melting curing or a combination thereof so as to form a porous metal structure or a porous array metal structure 201 on and directly contacting to the second surface 105b of the metal heat-dissipation layer 105 without damaging the roughed surface 101a of the polymer base 101. The porous metal structure or porous array metal structure has a thickness substantially ranging from 10 μm to 5000 μm. The metal powder is formed of such as titanium, gold, silver, iron or a combination thereof. The sintering process is such as selective laser sintering (SLS) or direct metal laser sintering (DMSL). The melting process is such as selective laser melting (SLM) or electron beam melting (EBM).

The metal layer (not shown), having superior biocompatibility for inducing tissue cells to grow on the porous metal structure or the porous array metal structure 201, will be fused with the tissues and will not be peeled off the implanted tissues. The polymer base 101 of the metal/polymer composite material 100 has an elastic modulus similar to human bone tissues to avoid the problems of stress shielding effect which occurs when the metal material is used alone.

According to another embodiment of the present disclosure, a metal/polymer composite material with heterojunction and a method for fabricating the same are provided. Firstly, a surface roughening treatment is performed to form a roughed surface with non-directional roughness on the polymer base. Then, a metal heat-dissipation layer conformally blanketing over the roughed surface is formed.

Since the metal heat-dissipation layer is formed on the polymer base by using a low-temperature coating (deposition) technology, the metal heat-dissipation layer will not cause damage to the polymer base. Furthermore, the metal heat-dissipation layer conformally blankets over a roughed surface with an isotropic surface roughness, such that the metal heat-dissipation layer and the polymer base can be tightly bonded at the heterojunction. Therefore, in subsequent high temperature process, the problem of the metal heat-dissipation layer being peeled off due to the polymer material layer being damaged by the concentration and penetration of thermal stress can be avoided, and the performance of the metal/polymer composite material can be improved.

To summarize, the metal/polymer composite material and the method for fabricating the same provided in the disclosure not only resolves the problems encountered in convention technology but at the same time overcomes the restrictions and drawbacks of the metal/polymer composite material currently available, so as to achieve the objects of the disclosure. In the conventional technology, the problems stress concentration and insufficient elasticity will occur if the metal material alone is used, and the problem of the supporting strength being too weak will occur if the polymer material alone is used.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A metal/polymer composite material, comprising:
   a polymer base having a roughed surface and a plurality of recesses on the roughed surface; wherein the roughed surface has an isotropic surface roughness;
   a metal heat-dissipation layer having a thickness greater than 150 μm conformally blanketing over the roughed surface, wherein the metal heat-dissipation layer has a first surface contacting the roughed surface and a second surface opposite to the first surface, and both of the first surface and the second surface extend into the recesses; and
   a porous metal structure having a thickness ranging from 10 μm to 5000 μm formed on and directly contacting to the second surface.

2. The metal/polymer composite material according to claim 1, wherein the isotropic surface roughness has an average surface roughness (Ra) ranging from 1 μm to 5 μm.

3. The metal/polymer composite material according to claim 1, wherein the polymer base has a dense area formed under the roughed surface.

4. The metal/polymer composite material according to claim 1, wherein each of the recesses has an aspect ratio ranging from 1 to 4000.

5. The metal/polymer composite material according to claim 1, wherein the metal heat-dissipation layer comprises titanium (Ti), gold (Gu), titanium alloy, cobalt-chromium alloy (Co—Cr), stainless steel or a combination thereof.

6. The metal/polymer composite material according to claim 1, wherein the metal heat-dissipation layer has a thickness ranging from greater than 150 μm up to 500 μm.

7. The metal/polymer composite material according to claim 1, wherein the polymer base comprises: polyether ether ketone (PEEK), carbon reinforced PEEK, polyetherketoneketo (PEKK), polyaryletherketone (PAEK), polymethyl methacrylate (PMMA), polyethylene terephthalate (PET), polylactide (PLA), polytetrafluoroethene (PTFE), polyethylene (PE) or a combination thereof.

* * * * *